(12) United States Patent
Echevarria Parres

(10) Patent No.: US 8,859,270 B2
(45) Date of Patent: Oct. 14, 2014

(54) PROCESS AND APPARATUS FOR EXTRACTING BIODIESEL FROM ALGAE

(76) Inventor: Antonio Jose de Jesus de San Juan Bosco Echevarria Parres, Yucatan (MX)

(*) Notice: Subject to any disclaimer, the term of this patent is extended or adjusted under 35 U.S.C. 154(b) by 480 days.

(21) Appl. No.: 12/999,794

(22) PCT Filed: Sep. 8, 2008

(86) PCT No.: PCT/MX2008/000122
§ 371 (c)(1),
(2), (4) Date: Apr. 14, 2011

(87) PCT Pub. No.: WO2009/154437
PCT Pub. Date: Dec. 23, 2009

(65) Prior Publication Data
US 2011/0189741 A1  Aug. 4, 2011

(30) Foreign Application Priority Data
Jun. 18, 2008  (MX) .................... MX/a/2008/007914

(51) Int. Cl.
*C12M 1/00* (2006.01)
*C12N 1/12* (2006.01)
(Continued)

(52) U.S. Cl.
CPC ............... *C12P 7/649* (2013.01); *C12M 23/06* (2013.01); *C10L 1/026* (2013.01); *C10G 2300/1014* (2013.01); *C11B 1/106* (2013.01); *C12M 21/02* (2013.01); *C12M 33/10* (2013.01); *C12M 47/06* (2013.01); *C12M 43/02* (2013.01); *C11B 1/04* (2013.01); *Y02E 50/13* (2013.01); *C11C 3/003* (2013.01); *C11B 3/16* (2013.01)
USPC .................. 435/292.1; 435/257.1; 435/289.1; 435/283.1; 435/307.1

(58) Field of Classification Search
CPC .. C10G 2300/1014; C10L 1/026; C11B 1/04; C11B 1/106; C11B 3/16; C11C 3/003; C12M 21/02; C12M 23/06; C12M 33/10; C12M 43/02; C12M 47/06; C12P 7/649; Y02E 50/13
USPC ............................................ 435/283.1–309.4
See application file for complete search history.

(56) References Cited

U.S. PATENT DOCUMENTS

2004/0159537 A1  8/2004  Maeda et al.
2005/0274065 A1  12/2005  Portnoff et al.
(Continued)

FOREIGN PATENT DOCUMENTS

EP           1 411 042 A1     4/2004
EP           1 975 393 A1     10/2008
WO      WO 2008134836 A2 *  11/2008
WO      WO 2008/151373 A1   12/2008

OTHER PUBLICATIONS

International Search Report of PCT/MX2008/000122 (Feb. 18, 2009).

*Primary Examiner* — Nathan Bowers
*Assistant Examiner* — Lydia Edwards
(74) *Attorney, Agent, or Firm* — Millen, White, Zelano & Branigan, P.C.

(57) ABSTRACT

The present invention relates to a system for cultivation of algae, extraction of lipids and transesterification of the lipids to obtain biodiesel. The system comprises three sections, that is to say cultivation, extraction and storage and reaction. In the lipid extraction area there is an ultrasonic reactor wherein the external walls of the alga are ruptured together with those of the oil sac to permit the extraction of lipids in the transesterification area there is also an ultrasonic reactor which ruptures the molecules of the fluid which passes therethrough to accelerate the reaction and render it almost immediate.

14 Claims, 4 Drawing Sheets

(51) Int. Cl.
  *C12M 3/00* (2006.01)
  *C12M 1/12* (2006.01)
  *C10L 1/02* (2006.01)
  *C11B 1/10* (2006.01)
  *C12M 1/26* (2006.01)
  *C12P 7/64* (2006.01)
  *C11B 1/04* (2006.01)
  *C11C 3/00* (2006.01)
  *C11B 3/16* (2006.01)

(56) References Cited

U.S. PATENT DOCUMENTS

| | | |
|---|---|---|
| 2006/0162245 A1 | 7/2006 | Porter et al. |
| 2006/0293533 A1* | 12/2006 | Iyer ........................ 554/174 |
| 2007/0048848 A1 | 3/2007 | Sears |
| 2008/0160593 A1 | 7/2008 | Oyler |
| 2008/0311649 A1* | 12/2008 | Cloud et al. ............... 435/292.1 |
| 2010/0218734 A1 | 9/2010 | Sugioka et al. |
| 2010/0330615 A1* | 12/2010 | Neto ........................... 435/42 |

* cited by examiner

PROCESS AND APPARATUS FOR EXTRACTING BIODIESEL FROM ALGAE

FIELD OF THE INVENTION

The present invention relates to a diesel extraction from algae, where the process starts from the stage of cultivation of algae, continues with the extraction of algae lipids and transformation of lipids in the final product extraction process.

BACKGROUND OF THE INVENTION

As we go near the post oil economy, the mixture of future emerging energies is increasingly more in the near future.

An element that is further added to these energies is oil produced by the algae, which unlike other sources contain up to 60% of oil by weight.

The alga requires very few elements to grow, water, nutrients and Sun, and produced in ponds or in closed circuits, it has the capacity to produce huge amounts of oil.

United States Patent Application US2008086939 refers to a system and method for the growth of the algae with photo improved efficiency. The system includes a reactor formed with a duct for growing cells of algae in a medium. Subsequently system provides methods through the pipeline to move medium to a default rate so that the algae cells efficiently convert solar energy into chemical energy, a plurality of barriers have been positioned in fluid flow. These barriers are separated by default distances to create von Karman vortex in the middle. As a result, algae flow to the fluid surface to receive solar energy at regular intervals of time. The system is open and considers a wheel of vanes to move the medium.

United States Patent Application US2008086939 refers to a system and method for algae growth with photo improved efficiency. The system includes a reactor formed with a duct for growing cells of algae in a medium. Subsequently, the system provides methods through the pipeline to move medium to a default rate so that the algae cells efficiently convert solar energy into chemical energy, a plurality of barriers have been positioned in fluid flow. These barriers are separated by default distances to create von Karman vortex in the middle. As a result the algae flow to the fluid surface to receive solar energy at regular intervals of time. The system is open and considers a wheel of vanes to move the medium.

United States Patent Application US2008086938 refers to a system and method for producing biofuel from pollutant flows for the growth of algae, which is completely different from the invention filed herein.

United States Patent Application US2008090284 refers to a system to process algae and obtain a biofuel. The document referred to a completely different process to that described in this invention.

United States Patent Application US2008090284 refers to a system to process algae and obtain a biofuel. The document referred to a completely different process to that described in this invention.

WO2008048861 document refers to a system and method for producing algae with a high oil content. This system as well as the previous ones, has as a principal difference being an open system.

WO2008060571 document refers to a method and compositions for the production and purification of biofuels from micro algae and plants. The process includes some of the varieties of algae with a high content of oils. The document differs from this invention that uses a nano-carbon material particle smaller than 500 nanometers in size.

U.S. Pat. No. 3,955,317 is a system for growing plants in a tubular structure of clear plastic, where the algae contains nutrients and a stream of carbon dioxide is passed therethrough. This invention is focused on food production and it is a horizontal structure.

The Patent Application Publication FR 20907311 refers to a system of cultivation of algae where algae found in a floating tubular system and has means to float on water or sea system. The system provides for dark and light areas. This invention nor nears the present invention.

U.S. Pat. No. 7,135,308 concerns a process for ethanol obtaining process from algae, which is completely different from the present invention.

United States Patent Application US20070048848 while relates to closed system for growing algae, the system includes bags with multiple layers including thermal barriers for regulating the algae temperature. Besides, the system includes several mechanisms for moving the fluid within the system and provides means for regulating temperature.

BRIEF DESCRIPTION OF THE INVENTION

Figures Description

Figure 1:
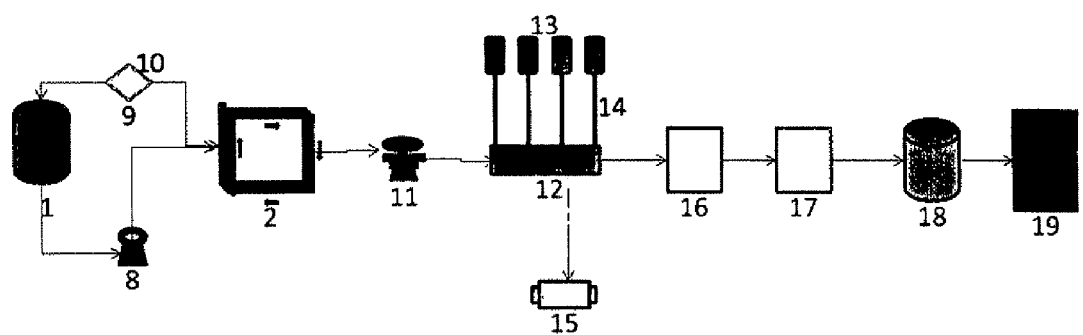
FIG. 1 is a simplified process flow diagram for growth and extraction section.
Figure 2:
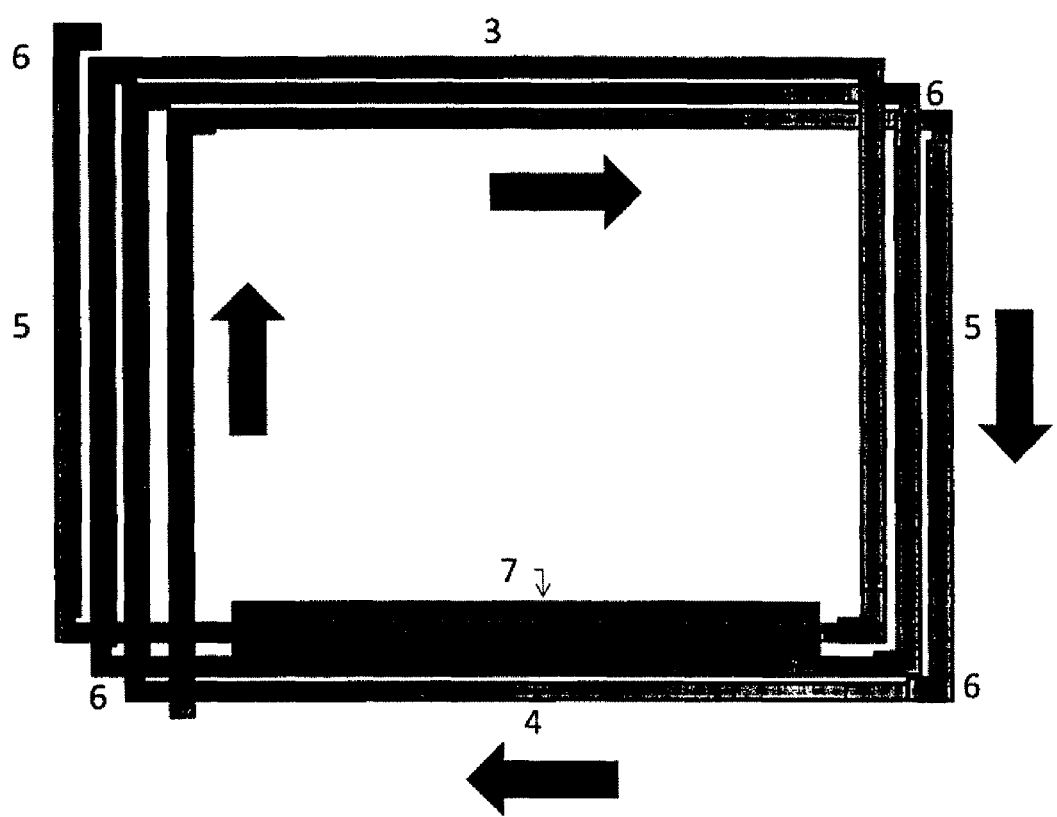
FIG. 2 is a perspective of growth reactor (2), drawing where jacket in the lower horizontal section (7) is shown.
Figure 3:
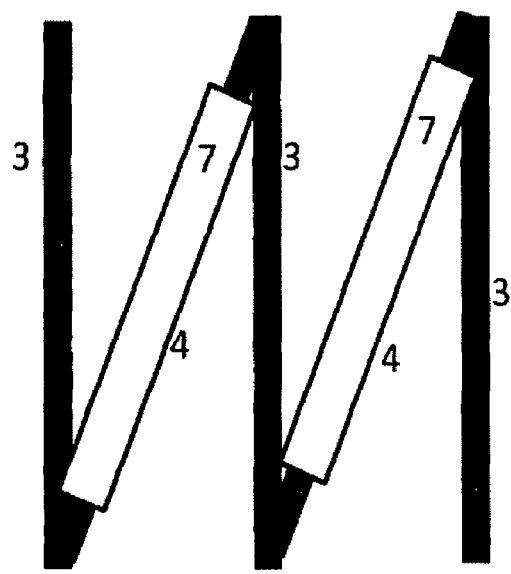
FIG. 3 is a top view of the growth reactor, where the lower horizontal sections (4) biased or displaced with respect to the upper ones are appreciated (3). Jacketed bottom or lower section is also appreciated (7).
Figure 4:
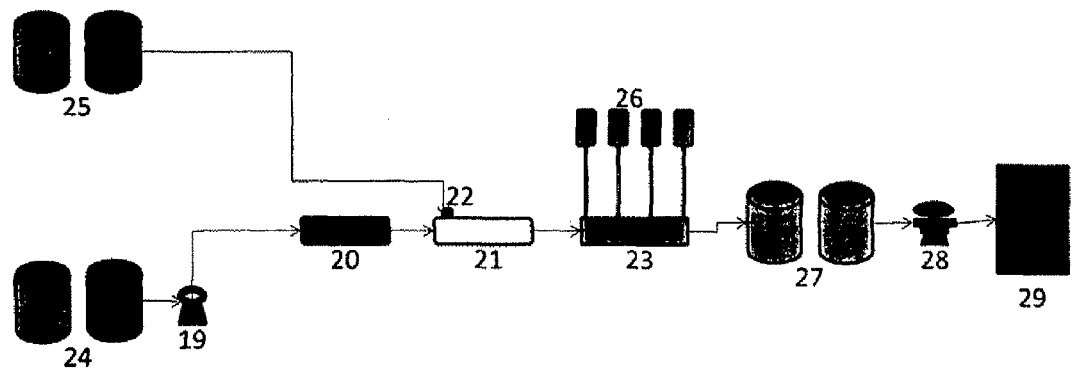
FIG. 4 is a simplified diagram of the process flow for biodiesel production process section.
Figure 5:
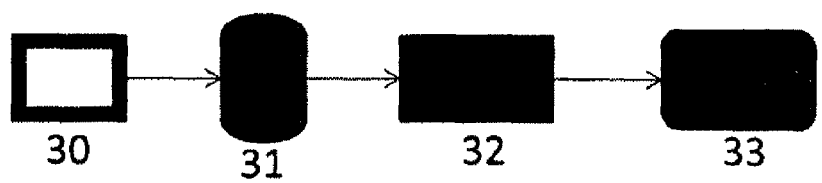
FIG. 5 is a simplified process flow diagram for the glycerin purification section.

The present invention relates to a system for the growth of algae, lipids extraction and transesterification of lipids for obtaining biodiesel. The system comprises three sections which are growing, extraction and storage and reaction.

Growth section consists of a mixture tank (1), a reactor of growth that consists of a continuous tubular structure (2) (closed system) in three dimensions that is comprised by clear tubular frames which in turn consist of horizontal upper sections (3) and lower (4) and vertical sections (5) where the frames are bonded in each section by 90 degrees elbows (6) and at the bottom of each frame, one of the elbows is displaced with respect to a vertical plane to allow continuity with the next frame, being parallel only the vertical sections, but not so the horizontal sections. Horizontal lower sections are coated by an opaque jacket (7) fed with water to keep medium temperature in an interval suitable for the growth of algae. Elbows and frames lower portion is opaque to give the algae periods of shadow and encourage growth. The material used may be plastic, glass, or any transparent and durable material. The system has a pump diaphragm (8) to move medium and a system of biomass detection (9) which is placed at the bottom of the growth reactor (2) that defines alga harvest time using two sensors (10) measuring medium density and light which passes through the medium.

To control production, the system has a number of sensors that are handled by a process control system or distributed control system (DCS), wherein a series of sensors act on pumps or valves to provide nutrients or allow gases or algae output from the closed system.

Tube length and diameter will depend directly from the growth reactor production capacity.

The system has a means to grow algae, which is comprised by a centrifuge (11) where algae and nutrients excess are separated. Algae is sent to a lipids extraction system which is a reactor (12) that operates with a series of ultrasound emitters (13) online. The number of emitters and reactor length depends on the amount and type of algae to be processed. The exposure area of the algae to the ultrasound within the reactor may be jacketed (14) to reduce algae temperature when being exposed to the treatment. In turn, extracted lipids are sent to a secondary extraction equipment (15) that may be an extraction equipment by compression or obtaining equipment through mixing with alcohol and one evaporator (16), for being subsequently sent to a centrifuge (17) that eliminates excess of water and further sent to storage tanks (18) where are sent to daily tanks for biodiesel production.

Processing system employs a pumping equipment (19) for transferring the oil to an online heater (20) and subsequently to the process reactor (23). It also has a static mixer (21) which has a port of entry (22) at the beginning of the mixer to generate turbulence and obtain a better mixing of oil with the catalyst which comes from the catalyzer tanks (25).

Reaction equipment consists of two daily tanks (24) and two catalyzer tanks (25). Being the number of variable tanks depending on the capacity plant. Reaction equipment (23) has a number of online ultrasound emitters (26). The geometry of the reactor is preferably tubular. There are two reservoir tanks (waiting period) (27) and a centrifuge (28) to separate the biodiesel from glycerol (28).

Biodiesel obtained is sent to a filters battery (29) with a polymer of cations exchange for its purification and glycerol is sent to a secondary system for treatment.

To treat glycerol obtained from the centrifuge, it is passed through a heat exchanger (30) where excess methanol is removed by evaporation, the secondary system has a process tank (31) and a press filter (32) to capture pollutants from glycerol. The system has also an electrodialysis equipment (33) comprised by electrodes and a series of anionic and cationic membranes alternately placed to eliminate salts of glycerol.

State of the art teachings prove that there is a large number of opportunities for obtaining diesel from plants and other living beings (biodiesel) processes can be summarized in oil extraction, reaction with methanol mixed with sodium hydroxide or potassium hydroxide (transesterification), washes with water to remove soaps and other impurities. One of the issues for biodiesel production is the speed with which results are obtained, which implies a greater energy consumption and increased production time. To eliminate this problem, the proposed system herein has, among other innovating concepts, with a system of extraction that uses ultrasound emitters to break the oil-containing sac in the algae, increasing extraction speed rate and decreasing the use of energy. Another contribution of this process involves the use of ultrasound to accelerate transesterification reaction; decreasing reaction time going from eight-hour to less than an hour, thus reaching its maximum efficiency, in the reaction over than 98 percent. Production process starts with filling in the bioreactor with water, nutrients and CO2; subsequently algae is sowed (500 liters of biomass) in the mixture (1) nutrients required in the medium are adjusted. Pumping is started from mixing tank (1) and recirculation in the bioreactor is started (2). If necessary, the distributed control system starts pumping hot or cold water towards bioreactor cooling jacket (7) to adjust temperature of the medium to a range of temperatures between 20 to 40 Centigrade. The algae may be *Neochloris oleoabundans, Chlorella vulgaris, Dunaliella Bioculata, Botryococcus Baunii*, etc., not limiting the algae for the described process.

Recirculation speed, residence time and growth rate vary according to the type of algae, as well as density and light absorbance, properties that determine the time of harvest.

To the algae return entry or input into the mixing tank, there is a three-way valve (not illustrated) regulated by light absorbance and culture medium density. When variables reach the established parameters (depending on every alga in particular) the three-way valve diverts flow to a centrifuge (11) that separates the excess water from biomass. Excess water is returned to the mixing tank (1) given that contains a large amount of nutrients and biomass is sent to the lipid extraction section.

To control our production we have a number sensors that are handled by our process control system, these sensors operating on pumps or valves for supplying nutrients or allow gases or algae output from the closed system.

These sensors are:
Dissolved oxygen sensor
Venting oxygen sensor
$CO_2$ sensor
Temperature sensor
pH sensor
Light sensor•conductivity sensor
Densimeter The amount of $CO_2$ that will be provided to the system, always will be of at least two-folded the weight of produced algae, since 50% of the algae is coal and carbon dioxide is 25% coal.

Nutrients to be provided will vary in relation to every alga in ranges less than 30%, however metals and vitamins will not vary.

As initial indicative range of nutrients will be as follows:
Na 15.5%
CA 8.1%
Mg 1.3%
P 19.1%
N 56%
Fe 0.65 mg l-1
Mn 0.05 mg l-1
Cu 2.5 µg
Zn 5 µg
Co 2.5 µg
Mo 2.5 µg
Thiamine 0.1 mg l-1
Biotin 0.5 µg/l
B12 0.5 µg/l Temperature range is kept between 20 and 40 Centigrade, preferably between 25 and 28 Centigrade.

pH will remain in a range from 8.2 to 8.7 through injection of some base such as sodium carbonate, sodium hydroxide, etc.

Depending on the type of algae, densimeter and light meter shall indicate when to harvest produced algae.

The extraction process starts with the pumping of biomass through the extraction equipment (12) that contains sound emitters (13), flowing online from one to another sound emission equipment, which work with an energy of 16000 W at 20 KHz. The number of emitters (13), its capacity, as well as the diameter of the reactor will depend on the biomass feeding, keeping the residence time in the extraction equipment for a period between one to two minutes. Sonic Energy will act on the algae outer walls and the algae oil sac inner wall creating micro implosions and explosions that finally manage to break the walls of the algae and the sac. In addition, another process to extract the oil remaining in the interior of the alga may be used. This additional process can be any of the already known customarily, either compression (15) or through capture with alcohols (16) for its subsequent evaporation. The product is finally sent to a centrifuge (17) for separation and sending by pipeline to process storage tanks (24).

The extracted oil is characterized according to following table:

| Composition of fatty acids (ISO5508/ISO5509) | |
|---|---|
| C 14:0 n-tetradecanoic | less than 0.1% |
| C 16:0 n-hexadecanoic | 8.0% |
| C 16:1 hexadecanoic | 0.2% |
| C 17:0 n-heptadecanoic | less than 0.1% |
| C 17:1 heptadecanoic | 0.1% |
| C 18:0 n-octadecanoic | 2.5% |
| C 18:1 octadecanoic | 39.9% |
| C 18:2 octadecadienoic (Omega 6) | 39.0% |
| C 18:3 alpha linolenic ALA (Omega 3) | 7.3% |
| C 18:4 octadecatetraenoic (Omega 3) | less than 0.1% |
| C 20:0 n-eicosanoic | 0.4% |
| C 20:1 eicosenoic | 0.8% |
| C 20:2 eicosadienoic | less than 0.1% |
| C 22:0 n-docosanoic | 0.4% |
| C 22:1 docosenoic | 0.1% |
| C 23:0 tricosanoic | less than 0.1% |
| C 24:0 tetracosanoic | 0.1% |
| C 22:6 docosahexaenoic DHA (Omega 3) | less than 0.1% |
| Saturated fatty acids | 11.7% |
| Monounsaturated fatty acids | 41.0% |
| Poly-unsaturated fatty acids | 46.6% |
| Fatty acids Omega 3 | 7.5% |
| Fatty acids, Omega 6 | 39.0% |
| Unknown fatty acids | 0.7% |

The algae exposure area to ultrasound may be jacketed (14) to decrease temperature of algae, being exposed to the treatment.

Transesterification process starts with pumping of oil from the storage tank (18) into the daily tank (24) (although a characterization of algae oil is already attached; in fact, any type of vegetable oil can be used in this process), fills the daily tank with the amount of oil necessary for processing in the shift and starts pumping of methanol to the online heater (20).

Catalysis tank (25) is filled with the methanol amount needed to process the oil up to 20% in volume against the oil tank (24) and potassium hydroxide 5% in granules is added. When potassium hydroxide is a in a 99% concentration. Blended until obtaining a perfect solution of potassium hydroxide in methanol.

Oil is pumped at a rate of 120 gallons per minute to the heater online (20) where it rises oil temperature to be processed at 50 Centigrade. This speed varies depending on the capacity plant.

At the same time, pumping the catalyst to the static mixer (21) is started, at a rate of 20% of the oil pumped, catalyst and oil start its mixture within the static mixer mixture port (22).

The product is pumped into a battery of sonication equipment (26) the number of emitters (26), its capacity, as well as the diameter of the process reactor (23) depend on the product feeding rate that will break oil molecule making that the reaction started at the static mixer port (22) accelerates and achieves during its passage in the production line. The number of ultrasound equipment (26) that is required will depend directly on the desired production volume.

In order to ensure 100% of the reaction, two reaction tanks (27) are placed with the necessary capacity to maintain four hours of production, at the end of the first tank filling, the second tank filling begins, to immediately send the product of the first tank to a centrifuge (28) that separates the Biodiesel from glycerol.

Biodiesel will be sent to a filters battery (29) with a acid cation exchange polymer in the form of hydrogen ions, that will clean impurities included and will give the finished product which is then stored.

Glycerol will be sent to a heat exchanger (30) for methanol extraction through evaporation. It is subsequently sent to a process tank (31) in presence of activated carbon, it will absorb or remove oils, color, odor, etc. The resulting product is sent to a filter press (32) to capture all pollutants.

As next step, glycerol is sent to electrodialysis process (33) consisting of electrodes and a series of anionic and cationic membranes alternately placed which in turn will act in the passage of electric current and glycerol by sending salts such as chlorides, sulphates, etc. to the anode and the species charged positively as sodium, will migrate towards the cathode, allowing thus to eliminate salts of the glycerol.

The only byproduct resulting from the entire process will be debris cake coming out of the filter press and a brine that will go out from electrodialysis process. This cake has fuel properties, so it can be used to develop another type of products through drying and molding as artificial firewood to mingle with flavoring essences.

The ASTM method specifications met by our Biodiesel B100 product are as follows: ASTM D 6751-02 requirements

| Property Units | Method | Limits |
|---|---|---|
| Flash point, cup closed | D 93 | 130 min ° C. |
| Water and sediments | D 2709 | 0.050 max % volume |
| Kinematic viscosity, 40° C. | D 445 | 1.9-6.0 mm2/s |
| Sulphated Ashes | D 874 | 0.020 max wt. % |
| Total sulphur | D 5453 | 0.05 max wt. % |
| Copper corrosion | D 130 | No. 3 max |
| Cetane Number | D 613 | 47 min |
| Cloud point | D 2500 | Customer report ° C. |
| Coal Residues | D 4530 | 0.050 max weight. % |
| Acid Number | D 664 | 0.80 max mgKOH/g |
| Free Glycerin | D 6584 | 0.020 weight. % |
| Total Glycerin | D 6584 | 0.240 weight. % |
| Phosphorus | D 4951 | 0.0010 weight. % |
| Vacuum distillation point | D 1160 | 360 max to ° C. 90% distillation |

Storage stability To be determined to be determined to be determined

Similarly, meets with European standard EN 14214

| Property | Units | Lower limit | Higher Lim | test Std |
|---|---|---|---|---|
| Esther content | % (m/m) | 96.5 | — | pr EN 14103d |
| Density at 15° C. | kg/m3 | 860 | 900 | EN ISO 3675/ EN ISO 12185. |
| Viscosity at 40° C. | mm²/s | 3.5 | 5.0 | EN ISO 3104 |
| Flashpoint | ° C. | >101 | — | ISO CD 3679e |
| Content of sulphur | mg/kg | — | 10 | — |
| Tar remnant | % (m/m) | — | 0.3 | EN ISO 10370 |
| Cetane number | | 51.0 | — | EN ISO 5165 |
| Sulfated ashes | % (m/m) | — | 0.02 | ISO 3987 |
| Water content | mg/kg | — | 500 | EN ISO 12937 |
| Total contamination | mg/kg | — | 24 | EN 12662 |
| Copper corrosion | Rating | Class 1 | Class 1 | EN ISO 2160 |

-continued

| Property | Units | Lower limit | Higher Lim | test Std |
|---|---|---|---|---|
| Thermal stability | — | — | — | — |
| Ox. Stability 110° C. | Hours | 6 | — | EN 14112 |
| Acid value | Mg KOH/g | — | 0.5 | Pr EN 14104 |
| Mudge value | — | — | 120 | Pr EN 14111 |
| Methyl Ester | % (m/m) | — | 12 | Pr EN 14103d |
| Methyl Ester (>=4 Dob lig) | % (m/m) | — | 1 | Pr EN 14103 |
| Methanol content | % (m/m) | — | 0.2 | Pr EN 141101 |
| Monoglycerides content | % (m/m) | — | 0.8 | Pr EN 14105m |
| Diglycerides content | % (m/m) | — | 0.2 | Pr EN 14105m |
| Triglycerides content | % (m/m) | — | 0.2 | Pr EN 14105m |
| Free glycerin | % (m/m) | — | 0.02 | Pr EN 14105m/pr |
| Total glycerin | % (m/m) | — | 0.25 | Pr EN 14105m |
| Base metals (Na + K) | Mg/kg | — | 5 | Pr EN 14108/pr |
| Phosphorus content | — | — | 10 | Pr EN14107p |

The invention claimed is:

1. System for obtaining diesel from algae comprising a growth section, and extraction section, and a reaction section,
said growth system comprising a primary mixer and a closed tubular bioreactor that receives fluid from the primary mixer,
said extraction section comprising a first centrifuge that receives fluid from the closed tubular bioreactor, a primary extractor that receives algae from the first centrifuge, a secondary extractor that receives extracted lipids from the primary extractor, a second centrifuge that receives oil from the secondary extractor, and
said reaction section comprising, a reactor wherein the reactor comprises at least two ultrasound emitters and wherein the reactor receives oil from the second centrifuge, a third centrifuge that receives oil from the reactor and a filter,
wherein the primary extractor is a continuous pipe wherein various energy emitters that generate ultrasound to break algae walls are located in the continuous pipe,
wherein the system additionally comprises storage tanks that receive oil from the second centrifuge, catalyst reaction tanks that receive oil from the storage tanks or second centrifuge, and daily tanks that receive oil from the storage tanks or second centrifuge,
wherein the reactor receives oil from the catalyst reaction tanks or the daily tanks,
wherein the reaction section additionally comprises an oil heater that receives oil from the daily tanks, a static mixer that receives heated oil from the oil heater and catalyst from the catalyzes tanks, and a continuous pipeline for receiving a mixture of oil and catalyst,
wherein various energy emitters that accelerate a transesterification reaction and generate ultrasound to break down oil components molecules are located in the continuous pipe, and
wherein the secondary extractor is a compressor capable of extracting oil.

2. The system of claim 1, wherein the secondary extractor is an evaporator.

3. The system of claim 1, wherein the bioreactor is comprises a system of clear tubular frames interconnected in a lower section of the bioreactor and fed by a diaphragm pump.

4. The system of claim 3, wherein the tubular frames are jacketed in the lower section.

5. The system of claim 1, wherein the energy emitters are jacketed.

6. A process for obtaining biodiesel from algae using the system of claim 1 wherein algae is sowed in a primary mixing tank, nutrients for algae growth are added and energy current is passed through a bioreactor comprised by tubular frames, where said frames lower section is jacketed and is opaque.

7. The process of claim 6, wherein temperature in the bioreactor is kept in a range from 20 to 40 centigrade.

8. A process of claim 6 where the energy current is recirculated towards the storage tank until obtaining a desired consistency determined by light absorbance and density.

9. A process of claim 8 where once the energy current reaches the specified conditions of absorbance and density, it is diverted through a three-way valve to a centrifuge to eliminate the excess of water, and is subsequently sent to a temporary storage tank where it is fed to a lipids extraction system.

10. The process of claim 9, where lipid extraction is performed by mixing with alcohol and subsequent evaporation.

11. The process of claim 9, wherein lipid extraction is performed—pH controlled—in a range from 8.2 to 8.7.

12. A method as in claim 9 where the lipids extraction involves a continuous pipeline where energy is passed through ultrasound emitters with a power range of 16000 W to 20 kHz to break inner and outer algae walls and oil sac enabling subsequent extraction using a compression process.

13. A process as in claim 12 where the oil obtained is sent to a centrifuge to be subsequently sent to biodiesel storage process tanks, and then the oil is sent to a heater and subsequently to a static mixer where it is mixed with a catalyst.

14. A process of claim 13 where the mixture is sent to the reactor where 16000 W to 20 kHz energy is applied to accelerate the reaction speed before the product (oil) obtained is sent to a centrifuge and subsequently to filtering tanks and product storage tanks.

* * * * *